United States Patent [19]

Simon et al.

[11] Patent Number: 4,622,316

[45] Date of Patent: Nov. 11, 1986

[54] 13-THIAPROSTAGLANDINS HAVING CYTOPROTECTIVE ACTIVITY

[75] Inventors: Bernd Simon, Dossenheim; Hanns-Gerd Dammann, Hamburg; Peter Müller, Heidelberg; Hans-Jürgen Legeler, Darmstadt-Eberstadt; Dieter Orth, Darmstadt; Hans-Eckart Radünz, Mühltal, all of Fed. Rep. of Germany

[73] Assignee: Merck Patent Gesellschaft mit beschränkter Haftung, Darmstadt, Fed. Rep. of Germany

[21] Appl. No.: 669,407

[22] Filed: Nov. 8, 1984

Related U.S. Application Data

[63] Continuation-in-part of Ser. No. 458,077, Jan. 14, 1983, abandoned.

[30] Foreign Application Priority Data

Jul. 14, 1982 [JP] Japan ................... 57-121354

[51] Int. Cl.[4] ................. A61K 31/615; A61K 31/215
[52] U.S. Cl. .................................. 514/162; 514/171; 514/420; 514/530
[58] Field of Search .............. 514/530, 162, 171, 420

[56] References Cited

U.S. PATENT DOCUMENTS 4,309,441  1/1982  Radunz et al. ............. 514/530

*Primary Examiner*—Sam Rosen
*Attorney, Agent, or Firm*—Millen & White

[57] ABSTRACT

13-thiaprostaglandins of Formula I

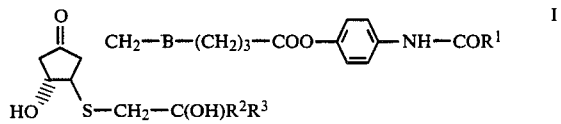

wherein
B is —$CH_2$—$CH_2$— or —CH=CH—,
$R^1$ is phenyl, $CH_3$, or $NH_2$,
$R^2$ is H or $CH_3$, and
$R^3$ is pentyl, hexyl, 1-methylpentyl, or 1,1-dimethylpentyl have valuable pharmacological properties, e.g., as cytoprotective agents.

20 Claims, No Drawings

13-THIAPROSTAGLANDINS HAVING CYTOPROTECTIVE ACTIVITY

This application is a continuation-in-part of U.S. Ser. No. 458,077, filed on Jan. 14, 1983, now abandoned and whose disclosure is incorporated by reference herein.

BACKGROUND OF THE INVENTION

It is known to combat lesions of the mucosa, especially of the upper gastrointestinal tract, using various pharmaceuticals. Above all, active agents from the group of the H$_2$-receptor antagonists are utilized for this purpose. Despite the widespread use of these compounds, they exhibit certain drawbacks in their application. The required doses are undesirably high, particularly for long-term therapy.

Also, it has been demonstrated in various studies that several natural and synthetic prostaglandins are capable of protecting, in low dosages, the mucous epithelium of the upper gastrointestinal tract (cf. A. Robert in: Advances in Ulcer Disease, Editors: K.-H. Holtermueller, J.-R. Malagelada, Excerpta Medica 1980: 72–77; Amsterdam-Oxford-Princton; Inn. Med. 9:35–38 [1982]). However, these compounds, especially the natural prostaglandins and derivatives very similar to them, are not devoid of side effects, either. Moreover, for several of these compounds, the cytoprotective properties are manifest at doses which do not preclude with certainty a protection of the mucosa due to acid inhibition which is observed at similar dosages. This permits only moderate separation of these biological activities.

SUMMARY OF THE INVENTION

Accordingly, it is an object of this invention to provide prostaglandin derivatives having advantageous properties, which can be used as cytoprotectively active pharmaceutical agents in combating lesions of the mucosa, which are readily compatible, which either lack the disadvantages of the conventional agents or exhibit them only to a minor extent, and which, in particular, have good separation of the most various biological activities, including separation of acid inhibition and cytoprotective effects.

Upon further study of the specification and appended claims, further objects and advantages of this invention will become apparent to those skilled in the art.

These objects have been achieved by this invention by providing pharmaceuticals having cytoprotective activity which contain cytoprotective 13-thiaprostaglandin derivatives of Formula I

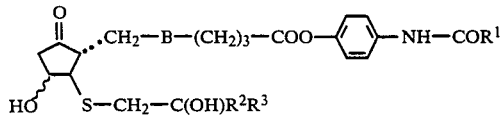

wherein
B is —CH$_2$—CH$_2$—or —CH=CH—,
R$^1$ is phenyl, CH$_3$, or NH$_2$,
R$_2$ is H or CH$_3$, and
R$_3$ is pentyl, hexyl, 1-methylpentyl, or 1,1-dimethylpentyl, as well as to a method of using these compounds in achieving cytoprotective effects, e.g., in combating mucosa lesions of the human and animal body.

It has been found that the 13-thiaprostaglandin derivatives of Formula I, with good compatibility, are capable, even at very low dosages, of protecting the mucous epithelium, especially of the upper gastrointestinal tract against a large number of ulcerogenic substances, such as acids and bases, concentrated ethanol, boiling water, certain pharmaceuticals, such as nonsteroidal antiphlogistics including acetylsalicylic acid and indomethacin, bile acids, such as sodium taurocholate, corticosteriods, and chemotherapeutical agents.

Accordingly, the invention relates to pharmaceuticals having cytoprotective activity which contain a 13-thiaprostaglandin derivative of the above-defined Formula I.

In this formula, a bond in the α-position is shown in dotted lines and a bond in the α-position in solid lines. Linkages which can be in the α- or β-position are characterized by a wavy line.

DETAILED DISCUSSION

These compounds, and processes for the preparation thereof, are known from U.S. Pat. No.4,309,441. whose disclosures are incorporated by reference herein. In this reference, several of the pharmacological effects of these compounds have also been described, especially their blood-pressure-lowering effects.

Furthermore, antisecretory properties with respect to gastric acid have also been disclosed therein. However, the disclosure of this reference does not permit the conclusion that these compounds also possess cytoprotective activity This cytoprotective, i.e., mucosa-protective effect, is an independent activity of these compounds and has nothing to do with the conventional antisecretory effect with respect to gastric acid. See, also, Mueller et al, Inn. Med., Vol 9, 35–38 (1982); Mueller et al, Lecture at Annual Scientific Meeting Luxembourg, 15–17th of April, 1982, inter alia; Dammann et al, Schweiz. med. Wschr, Vol 112, No. 23, 829–831, June 1982; and Mueller et al, Digestive Diseases and Sciences, Vol 27, No. 9, 862 (Sept. 1982); all of whose disclosures are incorporated by reference herein entirely.

Among the compounds of Formula I, those are especially preferred wherein B is —CH$_2$CH$_2$—, R$^1$ is phenyl, R$^2$ hydrogen or methyl, and R$^3$ is pentyl, 1-methylpentyl, or 1,1-dimethylpentyl. The pentyl and hexyl groups in the R$^3$ groups are preferably n-groups.

The hydroxy group on the five-membered ring is preferably in the α-position. The hydroxy group in the sulfur-containing side chain is preferably also in the α-position, but can also be β-positioned. The compounds can be present as racemates or racemic mixtures, and also in an optically active form. Especially preferred are 11α, 15-dihydroxy-15-methyl-9-oxo-13-thiaprostanoic acid p-benzoylaminophenyl ester (Ia) and 11α, 15-dihydroxy-15,16,16-trimethyl-9-oxo-13-thiaprostanoic acid p-benzoylaminophenyl ester.

The cytoprotective effects of these 13-thiaprostaglandin derivatives can be confirmed, for example, by conventionally measuring fecal blood loss under high-dosage antirheumatic therapy and prevention of such blood loss by simultaneous administration of at least one of these 13-thiaprostaglandin derivatives in low dosage. Another confirmation method involVes, for example, conventionally measuring the transmural potential difference after administration of so-called barrier breakers, such as acetylsalicylic acid in the presence and in the absence of these cytoprotective prostaglandins. This determination is based on the fact that the transmural potential difference, considered a measure of the functional integrity of the so-called mucosa barrier, falls after administration of mucosa-damaging irritants, such as acetylsalicylic acid, ethanol, or bile acids. This induced drop in potential difference can be prevented by previous or simultaneous administration of the prostaglandins of Formula I. Thus, in human patients, a dose of 0.7 μg/kg body weight of Ia, administered through gavage into the stomach, is capable of preventing a drop in transmural potential difference induced by administration of 1000 mg of acetylsalicylic acid. A similar positive effect on the potential difference otherwise caused by administration of 50 ml of 4 mmol/1 of sodium taurocholate can be achieved with 3.6 μg/kg body weight of Ia.

It is furthermore possible to prove cytoprotective efficacy by measuring the epithelial cell desquamation of the gastric mucosa by determining the DNA content in the gastric juice before and after administration of a so-called mucosa irritant. Thus, epithelial desquamation evoked by administration of relatively high-percentage ethanol or of acetylsalicylic acid can be prevented by simultaneous administration of and/or pretreatment with a prostaglandin of Formula I.

The invention furthermore concerns the use of 13-thiaprostaglandin derivatives of Formula I for the preparation of pharmaceuticals with cytoprotective activity, especially by nonchemical methods. In this connection, the active compounds can be brought into a suitable dosage form together with at least one solid, liquid and/or semi-liquid excipient or auxiliary agent and optionally in combination with one or more additional active ingredient(s).

These pharmaceuticals possessing cytoprotective activity can be utilized as medicinal agents in human or veterinary medicine for administration to mammals, including humans. Suitable excipients include organic or inorganic compounds amenable to enteral (e.g., oral), parenteral, or topical administration and inert with respect to the compounds of Formula I, for example, water, vegetable oils, benzyl alcohols, polyethylene glycols, glycerol triacetate, gelatin, carbohydrates, such as lactose or amylose, magnesium stearate, talc, etc. Especially suitable for oral administration are tablets, dragees, capsules, syrups, elixirs, or drops; for rectal administration, suitable are suppositories; for parenteral administration, solutions can be employed, preferably oily or aqueous solutions, furthermore suspensions, emulsions, or implants; suitable for topical application are ointments, creams, or powders. The compounds can also be lyophilized and the thus-obtained lyophilized products can be employed, for example, to prepare injection formulations. The indicated preparations can be sterilized and/or can contain auxiliary agents such as lubricants, preservatives, stabilizers and/or wetting agents, emulsifiers, salts to influence osmotic pressure, buffer compounds, colorants, flavoring agents and/or aromatous materials. They can also contain one or more additional active agents, if desired, for example one or more vitamins.

The invention furthermore relates to the use of 13-thiaprostaglandin derivatives of Formula I for protecting the tissue especially in the gastrointestinal zone (stomach, duodenum), but also in other regions of the human and animal body (e.g., liver, heart, brain), above all in combating lesions of cellular tissue, especially lesions of the mucosa, in particular mucosa lesions of the upper gastrointestinal tract induced by mucosa-irritating compounds, such as those mentioned above; as adjuvants in antirheumatic long-term therapy; for the prevention of stress-induced bleeding ulcers in acute and long-term therapy of peptic ulcers, especially of gastric ulcers, and also in gastritis of varying etiology, reflux esophagitis, excision gastritis after Billroth II operations, uremic gastritis, and furthermore for cytoprotection in conventional cytostatic therapy (stomatitis, cystitis, etc.).

Normally, the 13-thiaprostaglandin derivatives of Formula I are administered prophylactically or therapeutically in doses of 0.003 to 5 mg, especially 0.01 to 5 mg, above all 0.03 to 1 mg per dosage unit. The daily dose range is preferably 0.01 to 3 mg.

However, the specific dose for each individual patient depends on a great variety of factors, as usual, for example on the efficacy of the specific compound employed, on the age, body weight, general physical condition, sex, diet, etc. of the patient, on the time of administration and method of administration, on the rate of excretion, drug combination, and gravity of the respective disease to which the therapy is applied, etc. Oral administration is preferred.

As can be seen, the method of this invention includes both prophylactic and therapeutic administrations. The former will be indicated when a patient is diagnosed as especially susceptible, for example, to mucosa lesions of the upper gastrointestinal tract but the symptoms have not yet appeared. For example, prophylactic administration will be indicated when a patient susceptible to mucosa lesions will be taking a medicament which is a mucosa-irritating compound. Such prophylaxis can be conducted prior to or simultaneous with the administration of the irritant.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

The effects of the thiaprostaglandin Ia above (3-cis-hydroxy-2-trans-(3-methyl-3-hydroxy-1-heptyl-thio)-5-oxo-1-r-cyclopentylheptanoic acid-4-benzamidophenylester), on basal acid secretion as well as on aspirin- and bile salt-induced fall of gastric transmucosal potential difference (PD) in man, were measured.

Basal acid output was tested over a time period of 6 hr by intragastric titration with 0.1 N NaOH (N=6). Gastric potential difference was determined using the method of Anderson and Grossman, "Profile of pH, pressure and potential difference at gastroduodenal junction in man," Gastroenterology 49:364-369, 1965.

The compound Ia prevented the drop in gastric potential difference (control values $-42.4 \pm 2.8$ mV) associated with 1000 mg of aspirin and 50 ml of 4 mmol/liter sodium taurocholate. In control experiments, both irritants caused a fall in PD of about 30% within 10-15 min. (aspirin group $-29.1 \pm 2.4$ mV, sodium taurocholate group $-28.3 \pm 1.9$ mV). The protective dose against aspirin for Ia was 0.70 μg/kg body wt. Against sodium taurocholate, a dose of 3.6 μg/kg body wt. was effective.

By contrast, much higher doses of the tested prostaglandin analog were necessary to inhibit gastric acid secretion. For example, half-maximal inhibition of basal acid output was achieved by 20 μg/kg body wt. of Ia.

As can be seen, in analogy to animal findings, the prostaglandin analogs of this invention possess distinct cytoprotective properties in the human stomach in doses far below the antisecretory threshold.

The examples set forth below concern pharmaceutical preparations containing compounds of Formula I:

EXAMPLE A

Tablets

Tablets are pressed in the usual way so that each tablet contains 0.25 mg of Ia, 77 mg of lactose-monohydrate, 15 mg of cellulose, 6.75 mg of corn starch and 1 mg of magnesium stearate.

EXAMPLE B

Coated Tablets

Analogously to Example A, tablets are produced by press molding and then are coated in the usual way with a layer of saccharose, wheat starch, talc, tragacanth, and colorant.

EXAMPLE C

Hard Gelatine Capsules

Hard gelatine capsules are filled in the usual way so that each capsule contains 0.25 mg of Ia, 125 mg of lactose-monohydrate, 3 mg of cellulose and 1.75 mg of magnesium stearate.

EXAMPLE D

Soft Gelatine Capsules

Soft gelatine capsules are prepared in the usual way so that each capsule contains 0.25 mg of Ia and 99.75 mg medium-chain triglycerides USP.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of achieving a cytoprotective effect in a patient in need of such treatment, comprising administering to the patient an amount of a 13-thiaprostaglandin of the formula

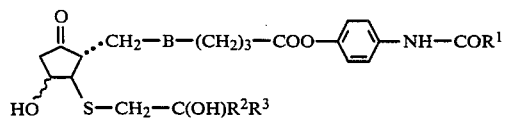

wherein
B is —$CH_2$—$CH_2$— or —CH=CH—,
$R^1$ is phenyl, $CH_3$, or $NH_2$,
$R^2$ is H or $CH_3$, and
$R^3$ is pentyl, hexyl, 1-methylpentyl, or 1,1-dimethylpentyl effective to achieve a cytoprotective effect but less than that required to achieve an antisecretory effect in said patient.

2. A method of claim 1 wherein the administration is prophylactic and the patient is not yet suffering from an abnormality treatable with a cytoprotective agent but is susceptible to such an abnormality which it is desired to prevent.

3. A method of claim 1 wherein the method is therapeutic and the patient is suffering from an abnormality treatable with a cytoprotective agent.

4. A method of claim 2 comprising co-administering to the patient a medicament which is cell tissue-irritating and a 13-thiaprostaglandin of said formula.

5. A method of claim 3 comprising co-administering to the patient a medicament which is cell tissue-irritating and a 13-thiaprostaglandin of said formula.

6. A method of claim 3 wherein the patient is suffering from a mucosa lesion of the upper gastrointestinal tract.

7. A method of claim 4 wherein said co-administered medicament is an irritant of the mucosa of the upper gastrointestinal tract.

8. A method of claim 2 wherein said abnormality to which the patient is susceptible is a peptic ulcer.

9. A method of claim 2 wherein said abnormality to which the patient is susceptible is gastritis.

10. A method of claim 4 wherein the co-administered medicament is a cytostatic agent.

11. A method of claim 1 wherein the daily dose is 0.01 to 3 mg.

12. A method of claim 1 wherein the 13-thiaprostaglandin is administered at a dosage at which it causes substantially no antisecretory effect.

13. A method of claim 1 wherein the 13-thiaprostaglandin is 11α, 15-dihydroxy-15-methyl-9-oxo-13-thiaprostanoic acid, p-benzoylaminophenyl ester or 11α, 15-dihydroxy-15,16,16-trimethyl-9-oxo-13-thiaprostanoic acid p-benzoylaminophenyl ester.

14. A composition of claim 13 wherein the 13-thiaprostaglandin is 11α, 15-dihydroxy-15-methyl-9-oxo-13-thiaprostanoic acid, p-benzoylaminophenyl ester or 11α, 15-dihydroxy-15,16,16-trimethyl-9-oxo-13-thiaprostanoic acid p-benzoylaminophenyl ester.

15. A method of claim 1, wherein the dosage is 0.03 to 1 mg.

16. A method of claim 11, wherein the dosage is 0.03 to 1 mg.

17. A pharmaceutical composition comprising (a) a medicament which is a cell tissue irritant and (b) an amount effective to achive a cytoprotective effect relative to that medicament of a 13-thiaprostaglandin of the formula

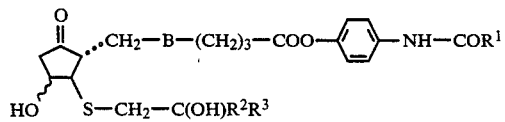

wherein
B is —$CH_2$—$CH_2$— or —CH=CH—,
$R^1$ is phenyl, $CH_3$, or $NH_2$,
$R^2$ is H or $CH_3$, and
$R^3$ is pentyl, hexyl, 1-methylpentyl, or 1,1-dimethylpentyl, 18. A pharmaceutical composition of claim 17 wherein the cell tissue irritant is a mucosa-irritant.

19. A pharmaceutical composition of claim 18 wherein the mucosa-irritating medicament is acetylsalicylinc acid, indomethacin, a bile acid or salt thereof, or a corticosteriod.

20. A pharmaceutical composition of claim 17 wherein the tissue-irritating medicament is a chemotherapeutical agent.

* * * * *